United States Patent [19]

Klein

[11] Patent Number: 5,396,881
[45] Date of Patent: Mar. 14, 1995

[54] FACIAL MASK AND METHOD OF USING SAME FOR TONING FACIAL MUSCLES

[76] Inventor: Sidi Klein, 5 Charoshet St., 47279 Ramat Hasharon, Israel

[21] Appl. No.: 132,336

[22] Filed: Oct. 6, 1993

[51] Int. Cl.⁶ ............................................. A61H 1/00
[52] U.S. Cl. ................. 601/23; 606/204.35; 2/206
[58] Field of Search ......... 128/24 R, 38, 66, DIG. 20; 606/204.35; 2/206, 425, DIG. 3

[56] References Cited

U.S. PATENT DOCUMENTS

| | | | |
|---|---|---|---|
| 495,265 | 4/1893 | Pinault | 2/206 |
| 809,360 | 1/1906 | Dible | 128/38 |
| 1,480,780 | 1/1924 | Pauley | 2/206 |
| 2,203,562 | 6/1940 | Edwards | 2/206 |
| 2,571,461 | 10/1951 | Livingston et al. | 128/DIG. 20 |
| 2,574,601 | 11/1951 | Swanson | 128/38 |
| 2,590,527 | 3/1952 | Fluck | 128/38 |
| 2,612,892 | 10/1952 | Beatman | 128/66 |
| 2,671,446 | 3/1954 | Mann | 606/204.35 |
| 2,923,291 | 2/1960 | Lagoma | 606/204.35 |
| 4,700,410 | 10/1987 | Westgate | 2/423 |

Primary Examiner—Edgar S. Burr
Assistant Examiner—Aaron J. Lewis
Attorney, Agent, or Firm—Benjamin J. Barish

[57] ABSTRACT

A facial mask for use in effecting toning of a wearer's facial muscles includes two spaced layers of flexible sheet material secured together along their outer margins, and a quantity of freely movable particles of a filling material in the space between the two layers. When the mask is to be worn, suction is applied to the space between the two layers in order to effectively rigidify the mask according to the configuration of the wearer's face. The mask is pressed against the wearer's facial muscles by pressurizing an expansible chamber engageable with the back of the wearer's head, and/or by pressurizing a chamber formed by the flexible sheet layer wall and a front rigid wall.

20 Claims, 3 Drawing Sheets

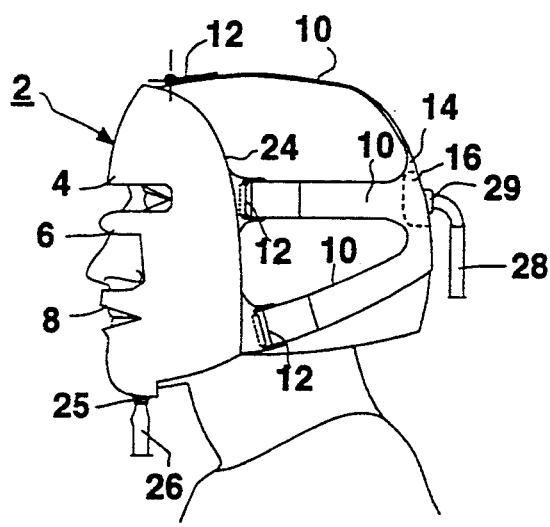
FIG. 1
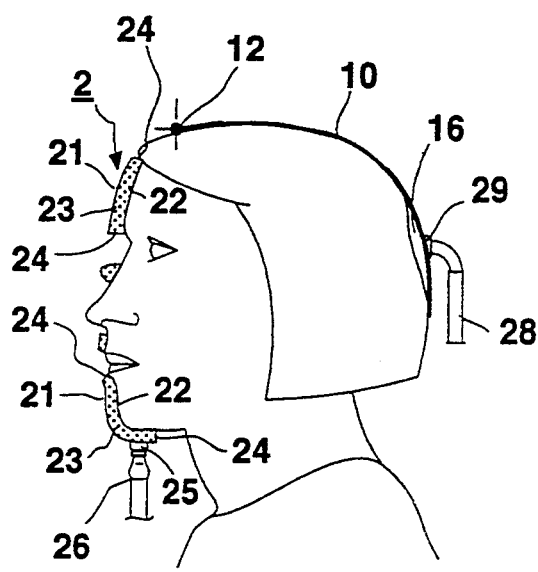
FIG. 2
FIG. 3
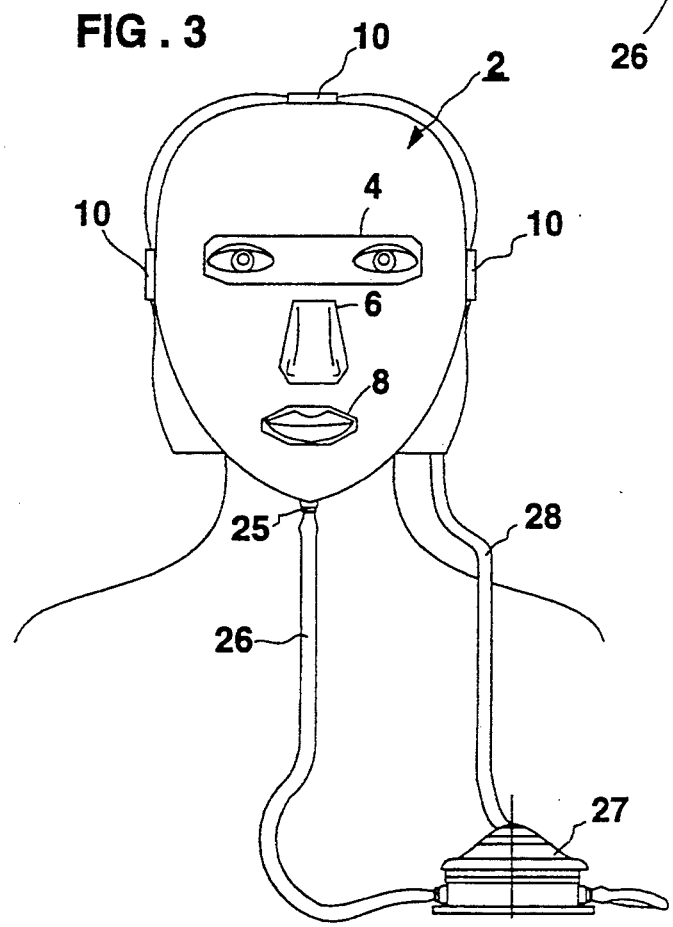

FACIAL MASK AND METHOD OF USING SAME FOR TONING FACIAL MUSCLES

RELATED APPLICATIONS

The present application is related to my U.S. patent application Ser. No. 07/078,633 filed Jul. 28, 1987, now U.S. Pat. No. 4,892,092, and is a continuation-in-part of my patent application Ser. No. 07/912,422 filed Jul. 13, 1992 which in turn is a continuation-in-part of my patent application Ser. No. 07/825,791 filed Jan. 21, 1992 (now abandoned), which in turn is a continuation of my patent application Ser. No. 07/319,244 filed Mar. 6, 1989 (now abandoned).

BACKGROUND OF THE INVENTION

The present invention relates to a facial mask, and also to a method of using such a mask for effecting isometric toning of facial muscles.

Lack of tone in the facial tissue and muscles contributes to facial sagging and skin wrinkling. One well-known muscle-toning technique is isometric exercise, wherein the muscle acts against resistance such that the muscle strain tends to cause the muscles to become toned. My U.S. Pat. No. 4,892,092 describes one form of facial mask which may be used for this purpose.

An object of the present invention is to provide another form of facial mask particularly, but not exclusively, useful for effecting isometric toning of facial muscles. Another object of the invention is to provide a method of effecting isometric toning of facial muscles.

BRIEF SUMMARY OF THE INVENTION

According to one aspect of the present invention, there is provided a facial mask comprising two spaced layers of flexible sheet material both of a configuration to cover a person's face, and having a quantity of freely movable particles of a filling material in between; and a suction device connected to the space between the two layers of flexible sheet material for drawing out the air from the space, after the mask has been applied to the face of a wearer, in order to effectively rigidify the mask according to the configuration of the wearer's face.

In the preferred embodiment of the invention described below, the facial mask further includes an expansible chamber carried at the rear of the mask to overlie the back of the wearer's head, such that when the chamber is expanded, it causes the mask to apply pressure to the wearer's facial muscles.

The filling material is preferably constituted of small particles of an expanded plastic. A preferred example is expanded polystyrene.

According to a further feature in one described embodiment, the layer of flexible sheet material on the side of the wearer's face includes a plurality of electrodes adapted to contact the wearer's skin. These electrodes sense EMG (electromyogram) signals produced by the muscles, and thereby provide an indication of whether the proper muscles are being exercised.

According to a further feature included in another described embodiment, the facial mask is used with an inflatable tube applied around the top of the wearer's head and under the wearer's chin. This tube is inflated to restrain up, down and side movements of the wearer's lower jaw with respect to the wearer's upper jaw during the use of the facial mask for toning the wearer's facial muscles. It has been found that the provision of such a restraining device decreases the electrical noise generated during the use of the mask, and thereby enables the mask to better sense the EMG signals produced by the muscles.

According to another aspect of the invention, there is provided a facial mask for use in effecting toning of a wearer's facial muscles, comprising: a flexible wall of flexible sheet material of a configuration to cover a person's face; a rigid wall secured to the outer margin of the flexible wall; and means for applying a compressed fluid to the space between the rigid wall and flexible sheet material wall for pressing the latter wall against the wearer's face.

The invention also provides a method of effecting toning of the facial muscles of a wearer, comprising: applying over the wearer's face a mask including two spaced layers of flexible sheet material having a quantity of freely movable particles of a filling material in between; drawing out the air from the space in order to rigidify the mask according to the configuration of the wearer's face; causing the mask to be firmly pressed against the wearer's face; and exercising the facial muscles.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a side elevational view illustrating one form of facial mask constructed in accordance with the invention;

FIG. 2 is a view similar to that of FIG. 1 but partially in section to show internal structure;

FIG. 3 is a front view of the facial mask of FIGS. 1 and 2;

DESCRIPTION OF PREFERRED EMBODIMENTS

The Embodiment of FIGS. 1–3

Figure 4:
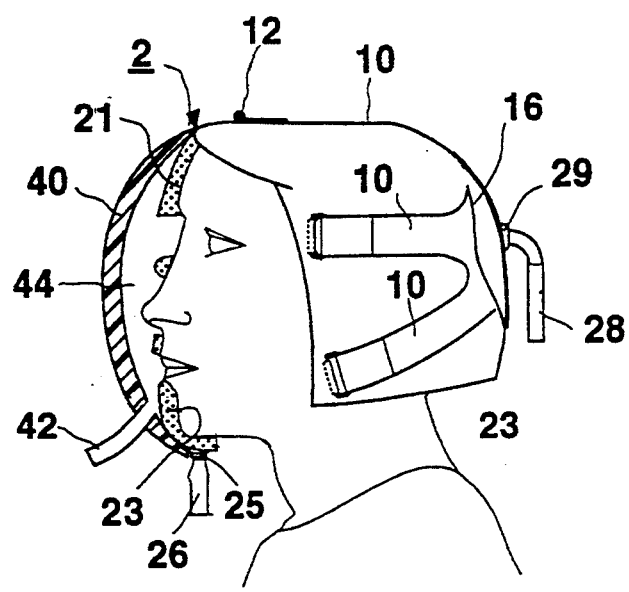
FIG. 4 is a view similar to that of FIG. 2, but illustrating a modification in the construction of the facial mask.

The facial mask illustrated in FIGS. 1–3 comprises a facial portion, generally designated 2, of the general configuration of a wearer's face, but formed with an elongated upper opening 4 for the wearer's eyes, an intermediate opening 6 for the wearer's nose, and a lower opening 8 for the wearer's mouth. The facial mask 2 further includes a plurality of straps 10 attachable to buckles 12 carried by the facial portion 2 for supporting the facial portion against the wearer's face. Straps 10 may be made of a single piece of elastic sheet material, e.g., rubber, cut to define a common central portion 14 formed with a plurality of radiating strips defining the straps 10. An expansible chamber 16 is carried by the central portion 14 of the straps so as to overlie and engage the back of the wearer's head when the facial mask is applied to the head of the wearer as illustrated in the drawings.

FIG. 2 more particularly illustrates the construction of the facial portion 2 of the mask. This portion comprises two spaced layers 21, 22 of flexible sheet material having a quantity of freely movable particles of a filling material 23 in between. The two sheets of flexible sheet material are joined together along their outer margins and also around the openings 4, 6 and 8 for the eyes, nose and mouth of the wearer, as shown at 24.

The facial portion 2 of the illustrated mask further includes a suction port 25 at the bottom of the facial portion leading to the space between the two layers of flexible sheet material 21, 22. Suction port 25 is connected via a tube 26 to the negative-pressure port of a manually-driven pump 27 (illustrated in FIG. 3). The positive-pressure port of pump 27 (FIG. 3) is connected by another tube 28 to a port 29 leading into the expansible chamber 16 carried at the rear end of the facial mask.

The filling material 23 in the space between the two layers of flexible sheet material 21, 22 in the facial portion 2 of the mask is constituted of relatively small, freely-movable particles, such as small particles of an expanded plastic. A preferred material for this purpose is small particles of expanded polystyrene having a particle size of a fraction of a millimeter or of a few millimeters. Thus, when the space between the two flexible sheet materials is at atmospheric pressure, the flexibility of the sheet materials, and the free mobility of the small particles of the filling material, impart a pliant nature to the facial portion 2 of the mask, permitting it to be applied to conform to the face of the wearer. However, by drawing out the air from the space between the two flexible sheets 21, 22 by the use of the pump 27, the facial portion 2 of the mask is rigidified according to the configuration of the wearer's face.

The facial mask illustrated in the drawings may be used in the following manner for affecting the toning of a person's facial muscles.

First, the mask is applied over the face of the wearer, and the buckles 12 are tightened to firmly press the facial portion 2 of the mask against the wearer's face. Pump 27 is then manually operated to draw out air from the space between the two flexible sheet layers 21, 22, thereby rigidifying the facial portion 2 of the mask according to the configuration of the wearer's face, as described above. Operation of the pump 27 also inflates the expansible chamber 16 at the rear of the mask, thereby causing the rigidified facial portion 2 to be firmly pressed against the wearer's face.

The wearer may then perform various isometric facial exercises which cause the muscles to act against the resistance produced by the mask, thereby toning the muscles. The Embodiment of FIGS. 4 and 5

Figure 5:
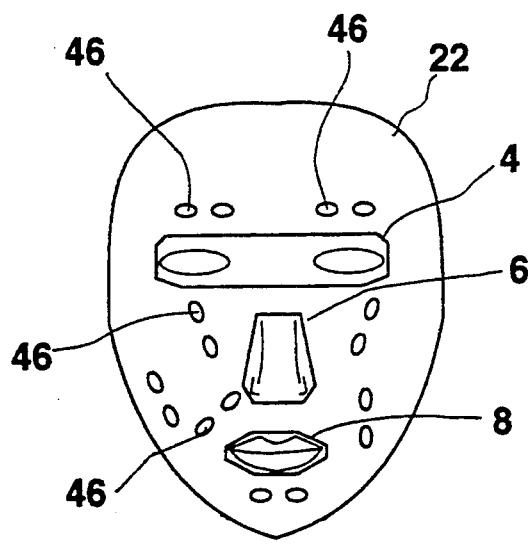
FIG. 5 is a view of the inside face of the facial mask of FIG. 4.

FIGS. 4 and 5 illustrate a modification in the construction of the facial mask of FIGS. 1-3. For the most part, the mask of FIGS. 4 and 5 is similarly constructed as in FIGS. 1-3, and therefore the same elements are correspondingly numbered to faciliate understanding.

The facial mask of FIGS. 4 and 5, however, includes a rigid wall 40 secured to the outer margin of the two spaced layers 21, 22, outwardly of the two layers when the mask has been applied to the face of a wearer, as shown in FIG. 4. Rigid wall 40 is of dome-shape and is made of a transparent plastic material so that the wearer can see, and be seen, through it.

The mask further includes a tube 42 leading to the space 44 between the rigid wall 40 and the two flexible layers 21, 22 for introducing into that space a compressed fluid, preferably compressed air, to press the two layers 21, 22 against the wearer's face. The inner surface of the inner layer 22 carries a plurality of electrodes, as shown at 46 in FIG. 5, near the openings 4, 6 and 8 for the eyes, nose and mouth of the wearer. These electrodes serve as surface electrodes for sensing EMG (electromyogram) signals produced by the muscles, to provide an indication of whether the proper muscles are being exercised.

The mask illustrated in FIGS. 4 and 5 is used in substantially the same manner as described above with respect to FIGS. 1-3, except that before the space between the two layers 21, 22 is evacuated in order to rigidify these two layers to the configuration of the wearer's face, the space 44 between the outer rigid wall 40 and the two layers 21, 22 is pressurized, e.g., by compressed air, in order to force the two layers 21, 22 firmly against the wearer's face and thus to more precisely fit the mask to the wearer's face, while at the same time applying some pressure to the wearer's face. After the space 44 has been thus pressurized, the space between the two layers 21, 22 is subjected to a vacuum, via tube 26, in order to rigidify the two layers to the configuration of the wearer's face, as described above.

Figure 6:
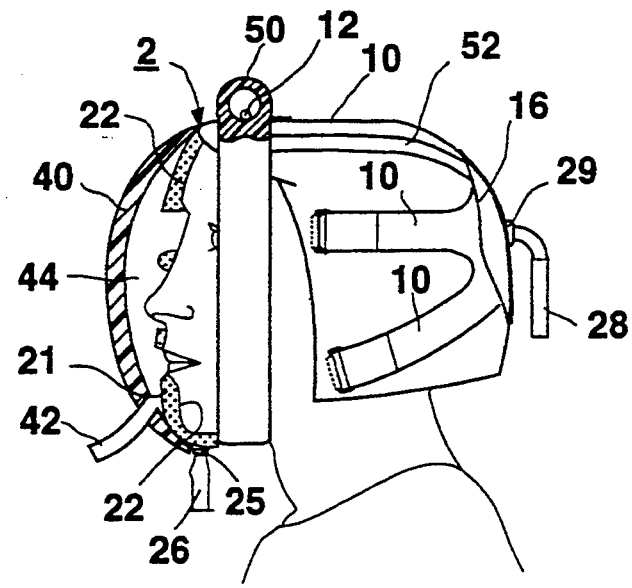
FIGS. 6 and 7 are views similar to those of FIGS. 4 and 5 but illustrating a further modification in the construction of the facial mask.
Figure 7:
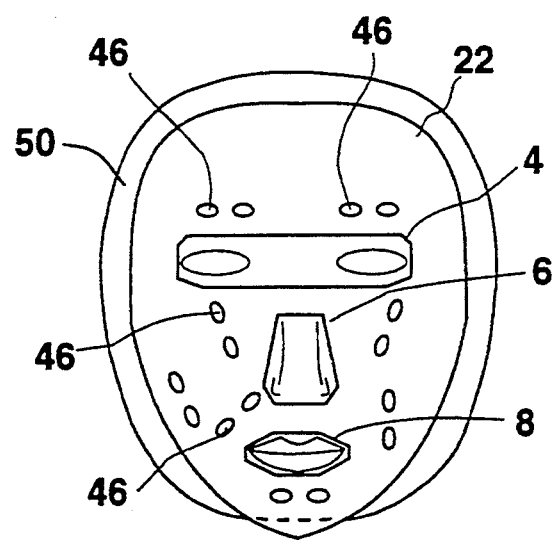

The Embodiment of FIGS. 6 and 7

FIGS. 6 and 7 illustrate a facial mask which is substantially the same as that illustrated in FIGS. 4 and 5, but which is provided with a restraining device for restraining up, down and side movements of the wearer's lower jaw, with respect to the wearer's upper jaw, during use of the facial mask for toning the wearer's facial muscles. To facilitate understanding, the elements in the facial mask of FIGS. 6 and 7 are identified by the same reference numerals as their corresponding elements in the facial mask of FIGS. 4 and 5.

The restraining device in the facial mask of FIGS. 6 and 7 is in the form of an inflatable tube 50 which is applied around the top of the wearer's head and under the wearer's chin during use of the facial mask. Tube 50 is inflated by a tubing 52 leading to the expansible chamber 16 (or to tube 28 or to tube 42) connected to the positive-pressure side of pump (27, FIG. 3).

Thus, when the facial mask is used to effect toning of the facial muscles, tube 50 is also inflated to thereby restrain up, down and side movements of the wearer's lower jaw with respect to the upper jaw. It has been found that this feature significantly decreases the noise signals picked-up by the electrodes 46. This feature better permits the electrodes to sense the true EMG (electromyogram) signals produced by the facial muscles, and thereby provides a better indication of whether the proper muscles are being exercised.

While the invention has been described with respect to three preferred embodiments, it will be appreciated that many variations may be made. For example, the mask could also include a mouthpiece to be inserted into the wearer's mouth and rigidified, or not rigidified by the suction. Also, the facial mask could be used for other purposes, e.g., to serve as a mould for reproducing the face or bust of a person. Many other variations, modifications and applications of the invention may be made.

What is claimed is:

1. A facial mask comprising two spaced layers of flexible sheet material both of a configuration to cover a person's face, and having a quantity of freely movable particles of a filling material in between; and a suction device connected to the space between said two layers of flexible sheet material for drawing out the air from said space, after the mask has been applied to the face of a wearer, in order to effectively rigidify the mask according to the configuration of the wearer's face.

2. The facial mask according to claim 1, further including an expansible chamber carried by the mask at the rear thereof to overlie the back of the wearer's head, such that when the chamber is expanded, it causes the mask to apply pressure to the wearer's facial muscles.

3. The facial mask according to claim 2, wherein said suction device includes a pump having a negative-pressure port connected to the space between said two layers of flexible sheet material for drawing out the air from said space, and a positive-pressure port connected to said expansible chamber.

4. The facial mask according to claim 3, wherein said pump is a manually-operated pump.

5. The facial mask according to claim 1, wherein said filling material is constituted of small particles of an expanded plastic.

6. The facial mask according to claim 5, wherein said filling material is constituted of small particles of expanded polystyrene.

7. The facial mask according to claim 1, wherein said mask covers substantially the complete face of the wearer but includes openings for the wearer's eyes, nose and mouth.

8. The facial mask according to claim 1, further including a rigid wall secured to the outer margin of said two spaced layers so as to be spaced outwardly of said layers when the mask has been applied to the face of a wearer, and means for applying compressed fluid to the space between said rigid wall and two spaced layers for pressing said two spaced layers against the wearer's face.

9. The facial mask according to claim 8, wherein said rigid wall is transparent.

10. The facial mask according to claim 1, wherein the layer of flexible sheet material on the side of the wearer's face includes a plurality of electrodes adapted to contact the wearer's skin.

11. A facial mask for use in effecting toning of a wearer's facial muscles, comprising:
a flexible wall of flexible sheet material of a configuration to cover at least a portion of a person's face and having an outer margin;
a rigid transparent wall secured to said flexible wall along the outer margin of the flexible wall to define a space between the two walls and to cover the person's complete face;
and a pressurising device for applying a compressed fluid to the space between said rigid wall and flexible wall for pressing said flexible wall against the wearer's face.

12. The facial mask according to claim 11, wherein the side of the flexible wall contacting the wearer's face when the mask is worn includes a plurality of electrodes adapted to contact the wearer's skin.

13. The facial mast according to claim 12, in combination with an inflatable tube to be applied around the top of the wearer's head and under the wearer's chin, and an inflating device for inflating the tube to cause it to restrain up, down and side movements of the wearer's lower jaw with respect to the wearer's upper jaw during use of the facial mask.

14. The facial mask according to claim 11, wherein said flexible wall includes two spaced layers of flexible sheet material and a quantity of freely movable particles of filling material in between the two spaced layers; said facial mask further including a suction device connected to the space between said two layers of flexible sheet material for drawing out the air from said space, after the mask has been applied to the face of a wearer, in order to effectively rigidify the mask according to the configuration of the wearer's face.

15. The facial mask according to claim 14, further including an expansible chamber carried by the mask at the rear thereof to coverlie the back of the wearer's head, such that when the chamber is expanded, it causes the mask to apply pressure to the wearer's facial muscles.

16. The facial mask according to claim 15, wherein said suction device includes a pump having a negative-pressure port connected to the space between said two layer of flexible sheet material for drawing out the air from said space, said pressurising device being a positive-pressure port of said pump which is also connected to said expansible chamber.

17. The facial mask according to claim 14, wherein said filling material is constituted of small particles of an expanded plastic.

18. A method of effecting toning of the facial muscles of a wearer, comprising:
applying over the wearer's face a mask comprising two spaced layers of flexible sheet material having a quantity of freely movable particles of a filling material in between;
drawing out the air from said space in order to rigidify the mask according to the configuration of the wearer's face;
causing the mask to be firmly pressed against the wearer's face; and
exercising the facial muscles.

19. The method according to claim 18, wherein the facial mask is caused to be firmly pressed against the wearer's face by inflating an expansible chamber carried by the mask and overlying the back of the wearer's head.

20. The method according to claim 18, wherein the facial mask includes a rigid wall secured to the outer margin of said two spaced layers so as to be spaced outwardly of said layers when the mask has been applied to the face of a wearer; and the facial mask is caused to be firmly pressed against the wearer's face by applying a compressed fluid to the space between said rigid wall and two spaced layers.

* * * * *